United States Patent [19]
Hirano et al.

[11] Patent Number: 5,308,726
[45] Date of Patent: May 3, 1994

[54] ELECTROPHOTOGRAPHIC PHOTOSENSITIVE ELEMENT

[75] Inventors: Akira Hirano; Eriko Tsuruoka, both of Tokyo, Japan

[73] Assignee: NEC Corporation, Tokyo, Japan

[21] Appl. No.: 989,817

[22] Filed: Dec. 14, 1992

[30] Foreign Application Priority Data

Dec. 12, 1991 [JP] Japan .................. 3-350778

[51] Int. Cl.$^5$ .............................. G03G 5/06
[52] U.S. Cl. ........................... 430/56; 430/59; 430/73; 430/74; 430/75; 430/76; 430/77
[58] Field of Search ............. 430/59, 73, 75, 77, 430/83, 74, 76, 56

[56] References Cited

U.S. PATENT DOCUMENTS

| | | | |
|---|---|---|---|
| 3,820,989 | 6/1974 | Rule et al. | 430/59 |
| 3,873,311 | 3/1975 | Contais et al. | 430/73 |
| 5,024,912 | 6/1981 | Neishi | 430/59 |

*Primary Examiner*—Christopher Rodee
*Attorney, Agent, or Firm*—Sughrue, Mion, Zinn, Macpeak & Seas

[57] ABSTRACT

An electrophotographic photosensitive element is here disclosed which comprises a conductive substrate and at least a photosensitive layer formed on the conductive substrate, the electrophotographic photosensitive element being characterized in that the photosensitive layer contains, as a charge transport material, a compound represented by the formula (1), (2) or (3)

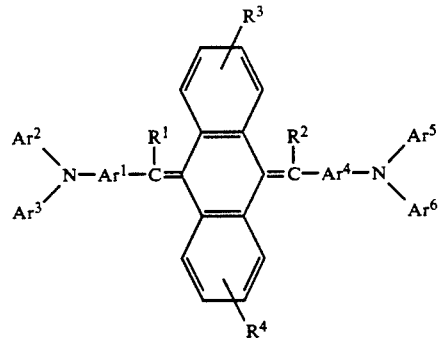

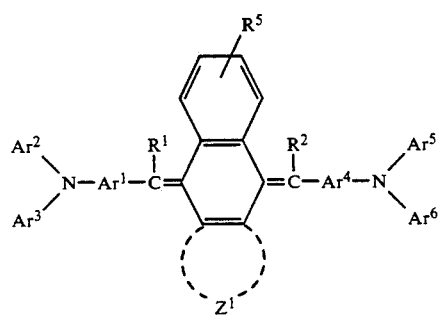

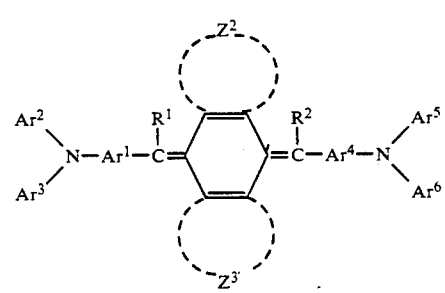

3 Claims, 3 Drawing Sheets

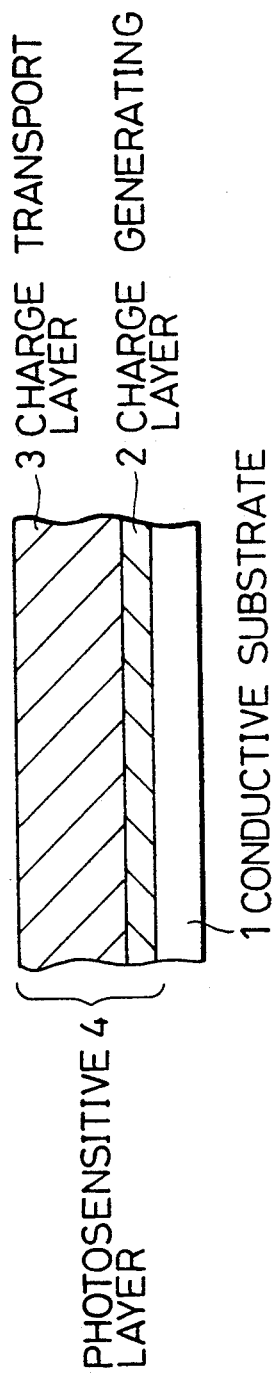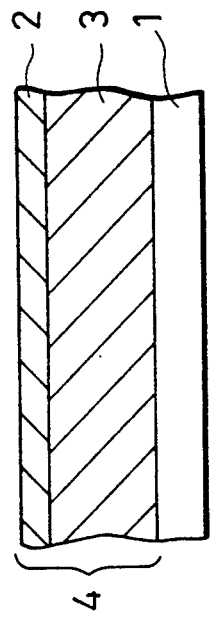

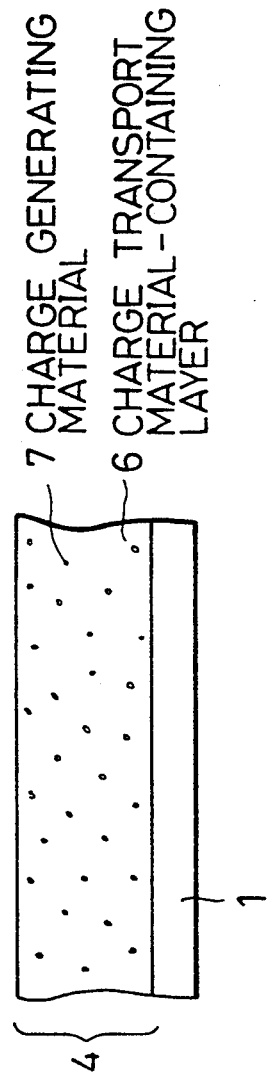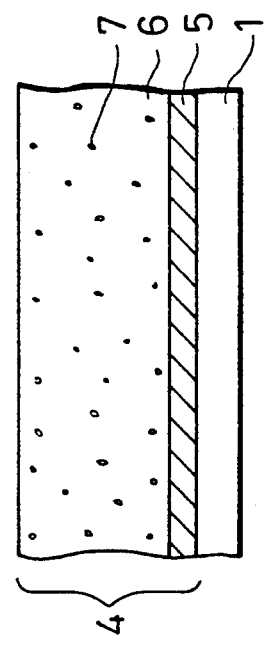

ELECTROPHOTOGRAPHIC PHOTOSENSITIVE ELEMENT

BACKGROUND OF THE INVENTION

1. Field of the Invention

The present invention relates to an electrophotographic photosensitive element, and more specifically, it relates to an electrophotographic photosensitive element equipped with a photosensitive layer containing a charge generating materials and a charge transport material.

2. Description of the Prior Art

As photoconductive materials of photosensitive elements which have been heretofore used in an electrophotographic system, there are inorganic materials such as selenium (Se), cadmium sulfide (CdS), zinc oxide (ZnO) and amorphous silicon (a-Si). These inorganic photosensitive elements have many advantages, but simultaneously they have various disadvantages such as being toxic, the difficulty of disposal and high cost. Therefore, in recent years, many organic photosensitive elements using organic materials which are free from these disadvantages have been suggested and already put into practice.

These photosensitive elements can be classified into a function separating type photosensitive element having a multi-layer structure in which a material for generating a charge carrier (hereinafter referred to as "charge generating material") and another material for receiving the generated charge carrier and transport it (hereinafter referred to as "charge transport material") are used in separate layers, and a single layer type photosensitive element in which the charge generation and the charge transport are carried out in one layer. In general, the function separating type photosensitive element is more often used because of having a wide selectable range of materials and being capable of heightening sensitivity.

As charge transport materials, there are a material using a photoconductive polymer such as a polyvinylcarbazole, and a material obtained by dispersing/dissolving a low-molecular photosensitive material in a binder polymer. The photoconductive polymer, when used singly, is insufficient in film forming ability and adhesive properties, and in order to improve these points, a plasticizer, a binder polymer and the like are used. However, the employment of these components may give rise to the deterioration of the sensitivity and the increase of residual surface potential, which are practical problems. On the other hand, in the case that the low-molecular photosensitive material is dispersed/dissolved in the binder polymer, the photosensitive element having excellent mechanical properties can easily be obtained by suitably selecting the polymer. However, the thus obtained photosensitive element is not considered to be sufficient in sensitivity and stability. For example, a diaryl alkane derivative described in U.S. Pat. No. 3,820,989 has little problem of compatibility with the binder polymer, but it is poor in stability to light. Thus, if this derivative is used for the photosensitive layer of the electrophotographic photosensitive element and then repeatedly subjected to charging and exposure, the sensitivity of the photosensitive element gradually deteriorates.

Furthermore, in the case that stilbene compounds described in Japanese Laid-open Application No. 65440/1983 are repeatedly used, stability is not satisfactory, though charge retention ability, sensitivity and the like are relatively good. In addition, these compounds have a problem regarding the sensitivity at low surface potential.

SUMMARY OF THE INVENTION

An object of the present invention is to provide an electrophotographic photosensitive element having excellent photosensitive properties and excellent surface potential stability at the time of repeating use by utilizing a charge transport material comprising a novel organic photoconductive material.

A first aspect of the present invention is directed to an electrophotographic photosensitive element comprising a conductive substrate and at least a photosensitive layer formed on the conductive substrate, said electrophotographic photosensitive element being characterized in that the photosensitive layer contains, as a charge transport material, a compound represented by the formula (1)

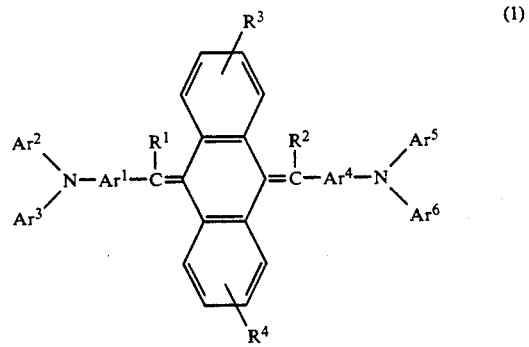

(wherein each of $Ar^1$, $Ar^2$, $Ar^3$, $Ar^4$, $Ar^5$ and $Ar^6$ is a mono or disubstituted or non-substituted aromatic or heterocyclic group except a case where all of them are phenyl groups or phenylene groups; and each of $R^1$, $R^2$, $R^3$ and $R^4$ is a substituted or non-substituted aromatic or heterocyclic group, a hydrogen atom, a halogen atom, a hydroxyl group, a substituted or non-substituted amino group, a lower alkoxy group having 1 to 6 carbon atoms which may have a substituent, or a lower alkyl group having 1 to 6 carbon atoms which may have a substituent).

A second aspect of the present invention is directed to an electrophotographic photosensitive element comprising a conductive substrate and at least a photosensitive layer formed on the conductive substrate, said electrophotographic photosensitive element being characterized in that the photosensitive layer contains, as a charge transport material, a compound represented by the formula (2)

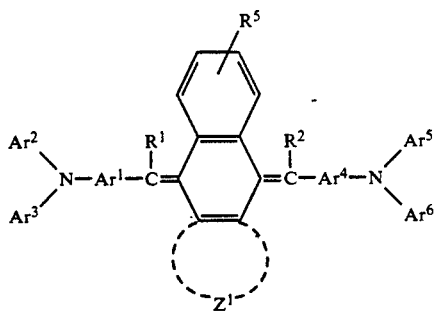

(2)

(wherein in —$Z^1$— is two hydrogen atoms, or a disubstituted or non-substituted heterocyclic group; each of $Ar^1$, $Ar^2$, $Ar^3$, $Ar^4$, $Ar^5$ and $Ar^6$ is a mono or disubstituted or non-substituted aromatic or heterocyclic group; and each of $R^1$, $R^2$ and $R^5$ is a substituted or non-substituted aromatic or heterocyclic group, a hydrogen atom, a halogen atom, a hydroxyl group, a substituted or non-substituted amino group, a lower alkoxy group having 1 to 6 carbon atoms which may have a substituent, or a lower alkyl group having 1 to 6 carbon atoms which may have a substituent).

A third aspect of the present invention is directed to an electrophotographic photosensitive element comprising a conductive substrate and at least a photosensitive layer formed on the conductive substrate, said electrophotographic photosensitive element being characterized in that the photosensitive layer contains, as a charge transport material, a compound represented by the formula (3)

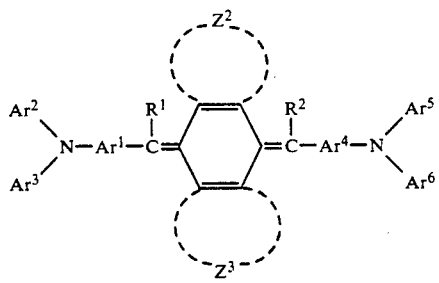

(3)

(wherein each of —$Z^2$— and —$Z^3$— is a disubstituted or non-substituted heterocyclic group; each of $Ar^1$, $Ar^2$, $Ar^3$, $Ar^4$, $Ar^5$ and $Ar^6$ is a mono or disubstituted or non-substituted aromatic or heterocyclic group; and each of $R^1$ and $R^2$ is a substituted or non-substituted aromatic or heterocyclic group, a hydrogen atom, a halogen atom, a hydroxyl group, a substituted or non-substituted amino group, a lower alkoxy group having 1 to 6 carbon atoms which may have a substituent, or a lower alkyl group having 1 to 6 carbon atoms which may have a substituent).

In addition, the present invention includes an electrophotographic photosensitive element in which the photosensitive layer has at least a charge generating layer and a charge transport layer, and the above-mentioned charge transport material is dispersedly present in the charge transport layer.

BRIEF DESCRIPTION OF THE DRAWINGS

FIGS. 1 to 6 are schematic sectional views illustrating embodiments of electrophotographic photosensitive elements of the present invention.

DETAILED DESCRIPTION OF THE INVENTION

Figure 3:
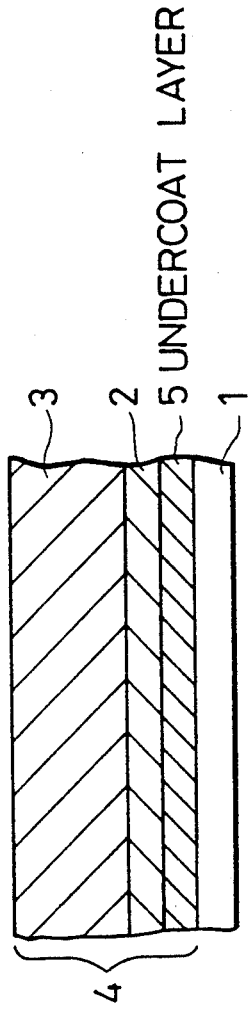

In the present invention, a compound represented by the above-mentioned formula (1), (2) or (3) is used as a charge transport material, and in the formula, each of —$Z^1$—, —$Z^2$— and —$Z^3$— is a disubstituted or non-substituted heterocyclic group and typical examples of the heterocyclic group include furan, thiophene, isooxazole and thiadiazole.

Each of $Ar^1$, $Ar^2$, $Ar^3$, $Ar^4$, $Ar^5$ and $Ar^6$ is a mono or disubstituted or non-substituted aromatic or heterocyclic group.

Examples of the aromatic group include phenyl, diphenyl, naphthyl and anthryl, and examples of the heterocyclic group include pyridyl, pyrrole, oxadiazole and thiophenyl.

Each of $R^1$ to $R^5$ is a substituted or non-substituted aromatic or heterocyclic group, a hydrogen atom, a halogen atom, a hydroxyl group, a substituted or non-substituted amino group, a lower alkoxy group having 1 to 6 carbon atoms which may have a substituent, or a lower alkyl group having 1 to 6 carbon atoms which may have a substituent.

Examples of the amino group include dimethylamino, diethylamino and diphenylamino; examples of the alkoxy group include methoxy, ethoxy, propoxy and butoxy; examples of the alkyl group include methyl, ethyl, propyl and butyl; and examples of the halogen atom include fluorine, chlorine, bromine and iodine.

The compounds represented by the formulae (1), (2) and (3) can be synthesized by a known procedure. For example, they can be obtained by condensing a phosphorous ester derivative represented by the formula (4)

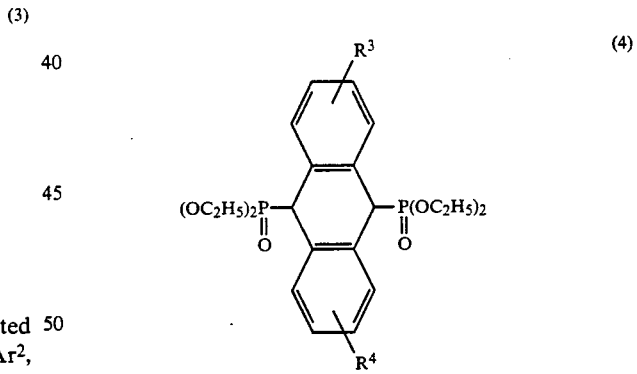

(4)

and an aldehyde derivative represented by the formula (5)

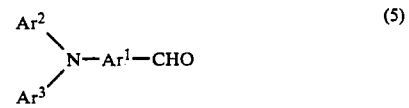

(5)

in accordance with the Wittig reaction.

Examples of the compounds having the formula (1) of the present invention are enumerated in Tables 1 to 7, those of the compounds having the formula (2) in Tables 8 to 12, and those of the compounds having the formula (3) in Tables 13 and 14. However, the compounds of the formulae (1), (2) and (3) should not be limited to the exemplified compounds.

TABLE 1

[Compounds represented by the formula (I)]

| Compound | Ar¹ | Ar² | Ar³ | Ar⁴ | Ar⁵ | Ar⁶ | $R^1$ | $R^2$ | $R^3$ | $R^4$ |
|---|---|---|---|---|---|---|---|---|---|---|
| 1 | biphenyl-yl | phenyl | phenyl | biphenyl-yl | phenyl | phenyl | H | H | H | H |
| 2 | biphenyl-yl | 4-CH₃-phenyl | 4-CH₃-phenyl | biphenyl-yl | 4-CH₃-phenyl | 4-CH₃-phenyl | H | H | 1-Cl | H |
| 3 | biphenyl-yl | 4-N(C₂H₅)₂-phenyl | 4-N(C₂H₅)₂-phenyl | biphenyl-yl | 4-N(C₂H₅)₂-phenyl | 4-N(C₂H₅)₂-phenyl | H | H | 2-N(C₂H₅)₂ | H |
| 4 | biphenyl-yl | 4-N(C₂H₅)₂-phenyl | 4-N(C₂H₅)₂-phenyl | biphenyl-yl | 4-N(C₂H₅)₂-phenyl | 4-N(C₂H₅)₂-phenyl | —CH₃ | —CH₃ | H | H |
| 5 | biphenyl-yl | 4-N(C₂H₅)₂-phenyl | 4-N(C₂H₅)₂-phenyl | biphenyl-yl | 4-N(C₂H₅)₂-phenyl | 4-N(C₂H₅)₂-phenyl | phenyl | phenyl | H | H |
| 6 | biphenyl-yl | 4-N(C₂H₅)₂-phenyl | 4-N(C₂H₅)₂-phenyl | biphenyl-yl | 4-N(C₂H₅)₂-phenyl | 4-N(C₂H₅)₂-phenyl | H | H | 2-t-C₄H₉ | H |
| 7 | biphenyl-yl | 4-N(C₂H₅)₂-phenyl | 4-N(C₂H₅)₂-phenyl | biphenyl-yl | 4-N(C₂H₅)₂-phenyl | 4-N(C₂H₅)₂-phenyl | H | H | 2-CH₃ | 7-CH₃ |

TABLE 2

Compounds represented by the formula (I)

| Compound | Ar¹ | Ar² | Ar³ | Ar⁴ | Ar⁵ | Ar⁶ | R¹ | R² | R³ | R⁴ |
|---|---|---|---|---|---|---|---|---|---|---|
| 8 | 4-biphenylyl | 4-(N,N-diethylamino)phenyl | 4-(N,N-diethylamino)phenyl | 4-biphenylyl | 4-methylphenyl | 4-methylphenyl | H | H | H | H |
| 9 | 4-biphenylyl | 4-(N,N-diethylamino)phenyl | 4-(N,N-diethylamino)phenyl | 4-biphenylyl | 3-chlorophenyl | phenyl | H | H | H | H |
| 10 | 4-biphenylyl | 3-methyl-4-(N,N-dimethylamino)phenyl | 4-(N,N-dimethylamino)phenyl | 4-biphenylyl | 3-chlorophenyl | phenyl | phenyl | phenyl | H | H |
| 11 | 4-biphenylyl | 3-(N,N-diethylamino)phenyl | phenyl | 4-biphenylyl | 3-(N,N-diethylamino)phenyl | 4-(N,N-diethylamino)phenyl | H | H | 2-CH₃ | H |
| 12 | 4-biphenylyl | phenyl | phenyl | 4-biphenylyl | 3-(N,N-diethylamino)phenyl | 4-(N,N-diethylamino)phenyl | H | H | 2-t-C₄H₉ | H |
| 13 | 4-biphenylyl | 4-methoxyphenyl | 4-methoxyphenyl | 4-biphenylyl | 4-methoxyphenyl | 4-methoxyphenyl | H | H | 2-C₂H₅ | H |
| 14 | 4-biphenylyl | 4-methoxyphenyl | 4-methoxyphenyl | 4-biphenylyl | 4-methoxyphenyl | 4-methoxyphenyl | phenyl | phenyl | H | H |

TABLE 3

[Compounds represented by the formula (1)]

| Compound | Ar¹ | Ar² | Ar³ | Ar⁴ | Ar⁵ | Ar⁶ | R¹ | R² | R³ | R⁴ |
|---|---|---|---|---|---|---|---|---|---|---|
| 15 | naphthyl | 4-MeO-C₆H₄ | 4-MeO-C₆H₄ | naphthyl | 4-MeO-C₆H₄ | 4-MeO-C₆H₄ | H | H | H | H |
| 16 | naphthyl | C₆H₅ | C₆H₅ | naphthyl | C₆H₅ | C₆H₅ | H | H | 2-N(C₂H₅)₂ | 7-N(C₂H₅)₂ |
| 17 | naphthyl | C₆H₅ | C₆H₅ | naphthyl | C₆H₅ | C₆H₅ | H | H | H | H |
| 18 | naphthyl | 3,4-(CH₃)₂-C₆H₃ | 3,4-(CH₃)₂-C₆H₃ | naphthyl | 3,4-(CH₃)₂-C₆H₃ | 4-CH₃-C₆H₄ | H | H | H | H |
| 19 | naphthyl | 4-MeO-C₆H₄ | 4-MeO-C₆H₄ | naphthyl | 4-MeO-C₆H₄ | 4-MeO-C₆H₄ | H | H | 1-Cl | H |
| 20 | naphthyl | 4-(Et₂N)-C₆H₄ | 4-(Et₂N)-C₆H₄ | naphthyl | 4-(Et₂N)-C₆H₄ | 4-(Et₂N)-C₆H₄ | H | H | H | H |

TABLE 4

Compounds represented by the formula (1)

| Compound | Ar¹ | Ar² | Ar³ | Ar⁴ | Ar⁵ | Ar⁶ | R¹ | R² | R³ | R⁴ |
|---|---|---|---|---|---|---|---|---|---|---|
| 21 | naphthyl | 4-CH₃-C₆H₄-N(C₂H₅)₂ | 4-CH₃-C₆H₄-N(C₂H₅)₂ | naphthyl | 4-CH₃-C₆H₄-N(C₂H₅)₂ | 4-CH₃-C₆H₄-N(C₂H₅)₂ | —CH₃ | —CH₃ | H | H |
| 22 | naphthyl | 4-CH₃-C₆H₄-N(C₂H₅)₂ | 4-CH₃-C₆H₄-N(C₂H₅)₂ | naphthyl | 4-CH₃-C₆H₄-N(C₂H₅)₂ | 4-CH₃-C₆H₄-N(C₂H₅)₂ | C₆H₅ | C₆H₅ | H | H |
| 23 | naphthyl | 4-CH₃-C₆H₄-N(C₂H₅)₂ | 4-CH₃-C₆H₄-N(C₂H₅)₂ | naphthyl | 4-CH₃-C₆H₄-N(C₂H₅)₂ | 4-CH₃-C₆H₄-N(C₂H₅)₂ | H | H | 2-t-C₄H₉ | H |
| 24 | naphthyl | 4-CH₃-C₆H₄-N(C₂H₅)₂ | 4-CH₃-C₆H₄-N(C₂H₅)₂ | naphthyl | 4-CH₃-C₆H₄-N(C₂H₅)₂ | 4-CH₃-C₆H₄-N(C₂H₅)₂ | H | H | 1-CH₃ | 7-CH₃ |
| 25 | naphthyl | C₆H₅ | C₆H₅ | naphthyl | C₆H₅ | C₆H₅ | H | H | 2-CH₃ | 2-t-C₄H₉ |
| 26 | naphthyl | pyridyl | pyridyl | naphthyl | pyridyl | pyridyl | H | H | H | H |

TABLE 5

[Compounds represented by the formula (1)]

| Compound | Ar¹ | Ar² | Ar³ | Ar⁴ | Ar⁵ | Ar⁶ | R¹ | R² | R³ | R⁴ |
|---|---|---|---|---|---|---|---|---|---|---|
| 27 | 2-methylnaphthyl | 3,5-dimethylphenyl | 3,5-dimethylphenyl | 3,5-dimethylphenyl | 3,5-dimethylphenyl | 3,5-dimethylphenyl | H | H | H | H |
| 28 | 2-methylnaphthyl | 4-(N,N-diethylamino)-methylphenyl | 4-(N,N-diethylamino)-methylphenyl | 3,5-dimethylphenyl | 4-(N,N-diethylamino)-methylphenyl | 4-(N,N-diethylamino)-methylphenyl | H | H | H | H |
| 29 | 2-methylnaphthyl | phenyl | phenyl | 3,5-dimethylphenyl | phenyl | phenyl | phenyl | phenyl | H | H |
| 30 | phenyl | naphthyl | phenyl | phenyl | naphthyl | phenyl | H | H | H | H |
| 31 | phenyl | naphthyl | 4-(N,N-diethylamino)-methylphenyl | phenyl | naphthyl | 4-(N,N-diethylamino)-methylphenyl | H | H | H | H |
| 32 | phenyl | naphthyl | 4-methylphenyl | phenyl | naphthyl | 4-methylphenyl | —CH₃ | —CH₃ | H | H |

TABLE 6

[Compounds represented by the formula (1)]

| Compound | Ar¹ | Ar² | Ar³ | Ar⁴ | Ar⁵ | Ar⁶ | $R^1$ | $R^2$ | $R^3$ | $R^4$ |
|---|---|---|---|---|---|---|---|---|---|---|
| 33 | phenyl | naphthyl | phenyl | phenyl | naphthyl | phenyl | H | H | 2-CH₃ | 7-CH₃ |
| 34 | phenyl | 2-methylnaphthyl | 4-methylphenyl | phenyl | 2-methylnaphthyl | 4-methylphenyl | H | H | H | H |
| 35 | phenyl | 2-methylnaphthyl | 2-methylnaphthyl | phenyl | 2-methylnaphthyl | 2-methylnaphthyl | H | H | H | H |
| 36 | phenyl | naphthyl | naphthyl | phenyl | naphthyl | naphthyl | —CH₃ | —CH₃ | H | H |
| 37 | phenyl | biphenyl | 4-methylphenyl | phenyl | biphenyl | 4-methylphenyl | H | H | H | H |
| 38 | phenyl | biphenyl | 2-methylnaphthyl | phenyl | biphenyl | 2-methylnaphthyl | H | H | H | H |
| 39 | phenyl | biphenyl | biphenyl | phenyl | biphenyl | biphenyl | H | H | 2-C₂H₅ | 7-C₂H₅ |
| 40 | biphenyl | 4-(N,N-dimethylamino)phenyl | biphenyl | biphenyl | 4-(N,N-dimethylamino)phenyl | biphenyl | H | H | H | H |

TABLE 7

Compounds represented by the formula (1): structural table for compounds 41–47 showing substituents Ar¹, Ar², Ar³, Ar⁴, Ar⁵, Ar⁶ and R¹, R², R³, R⁴ (all H).

TABLE 8

[Compounds represented by the formula (2)]

| Compound | Ar¹ | Ar² | Ar³ | Ar⁴ | Ar⁵ | Ar⁶ | R¹ | R² | R³ | Z¹ |
|---|---|---|---|---|---|---|---|---|---|---|
| 48 | 4-tolyl | 4-tolyl | 4-tolyl | phenyl | 4-tolyl | 4-tolyl | H | H | H | methylisoxazolyl |
| 49 | 4-tolyl | 4-(N,N-diethylamino)phenyl | 4-tolyl | 4-tolyl | 4-(N,N-diethylamino)phenyl | 4-tolyl | H | H | H | methylisoxazolyl |
| 50 | 4-tolyl | 1-naphthyl | 4-tolyl | phenyl | 1-naphthyl | 4-tolyl | phenyl | phenyl | H | methylisoxazolyl |
| 51 | 1-naphthyl | 4-ethylphenyl | 4-ethylphenyl | 4,5-naphthylene | 4-ethylphenyl | 4-ethylphenyl | H | H | H | methylisoxazolyl |
| 52 | 4-biphenyl | 4-tolyl | 4-tolyl | 4-biphenyl | 4-tolyl | 4-tolyl | H | H | H | methylisoxazolyl |
| 53 | 1-naphthyl | 4-tolyl | 1-naphthyl | 4,5-naphthylene | 4-tolyl | 1-naphthyl | H | H | H | methylisoxazolyl |

TABLE 9

[Compounds represented by the formula (2)]

| Compound | Ar¹ | Ar² | Ar³ | Ar⁴ | Ar⁵ | Ar⁶ | R¹ | R² | R³ | Z¹ |
|---|---|---|---|---|---|---|---|---|---|---|
| 54 | C₆H₄- | 4-CH₃-C₆H₄ | 4-CH₃-C₆H₄ | C₆H₄ | 4-CH₃-C₆H₄ | 4-CH₃-C₆H₄ | H | H | 2-CH₃ | furan |
| 55 | C₆H₄- | 4-CH₃-naphthyl | 4-CH₃-naphthyl | C₆H₄ | 4-CH₃-naphthyl | 4-CH₃-naphthyl | H | H | H | furan |
| 56 | C₆H₄- | 4-OCH₃-C₆H₄ | 4-OCH₃-C₆H₄ | C₆H₄ | 4-OCH₃-C₆H₄ | 4-OCH₃-C₆H₄ | H | H | H | furan |
| 57 | C₆H₄- | biphenyl | C₆H₅ | C₆H₄ | biphenyl | C₆H₅ | H | H | H | furan |
| 58 | biphenyl | 4-CH₃-C₆H₄ | 4-CH₃-C₆H₄ | biphenyl | 4-CH₃-C₆H₄ | 4-CH₃-C₆H₄ | H | H | 2-i-C₃H₇ | thiophene |
| 59 | biphenyl | 4-(N(C₂H₅)₂)-C₆H₄ | 4-(N(C₂H₅)₂)-C₆H₄ | biphenyl | 4-(N(C₂H₅)₂)-C₆H₄ | 4-(N(C₂H₅)₂)-C₆H₄ | H | H | H | thiophene |

TABLE 10

[Compounds represented by the formula (2)]

| Compound | Ar¹ | Ar² | Ar³ | Ar⁴ | Ar⁵ | Ar⁶ | R¹ | R² | R⁵ | Z¹ |
|---|---|---|---|---|---|---|---|---|---|---|
| 60 | naphthyl | 4-Cl-phenyl | naphthyl | naphthyl | 4-Cl-phenyl | naphthyl | H | H | H | thiophene |
| 61 | naphthyl | 4-CH₃-phenyl | phenyl | naphthyl | 4-CH₃-phenyl | phenyl | H | H | H | thiadiazole |
| 62 | naphthyl | biphenyl | phenyl | naphthyl | biphenyl | phenyl | H | H | H | thiadiazole |
| 63 | phenyl | 4-(N(CH₃)₂)-phenyl | 4-(N(CH₃)₂)-phenyl | phenyl | 4-(N(CH₃)₂)-phenyl | 4-(N(CH₃)₂)-phenyl | H | H | H | thiadiazole |
| 64 | phenyl | naphthyl | phenyl | phenyl | naphthyl | phenyl | —CH₃ | —CH₃ | 2-CH₃ | thiadiazole |
| 65 | naphthyl | phenyl | phenyl | naphthyl | phenyl | phenyl | H | H | H | thiadiazole |

TABLE 11

| Compound | Ar¹ | Ar² | Ar³ | Ar⁴ | Ar⁵ | Ar⁶ | R¹ | R² | R⁵ | Z¹ |
|---|---|---|---|---|---|---|---|---|---|---|
| 66 | C₆H₄ | 4-CH₃-C₆H₄ | 4-CH₃-C₆H₄ | C₆H₄ | 4-CH₃-C₆H₄ | 4-CH₃-C₆H₄ | H | H | H | furan |
| 67 | biphenyl | 3-CH₃-C₆H₄ | 3-CH₃-C₆H₄ | biphenyl | 3-CH₃-C₆H₄ | 3-CH₃-C₆H₄ | H | H | H | furan |
| 68 | naphthyl | 3-CH₃-C₆H₄ | 3-CH₃-C₆H₄ | naphthyl | 3-CH₃-C₆H₄ | 3-CH₃-C₆H₄ | H | H | H | thiophene |
| 69 | C₆H₄ | naphthyl | naphthyl | C₆H₄ | naphthyl | naphthyl | C₆H₅ | C₆H₅ | H | methyl-thiophene |
| 70 | C₆H₄ | 4-OCH₃-C₆H₄ | 4-OCH₃-C₆H₄ | C₆H₄ | 4-OCH₃-C₆H₄ | 4-OCH₃-C₆H₄ | H | H | H | isoxazole |
| 71 | C₆H₄ | 4-N(C₂H₅)₂-C₆H₄ | 4-N(C₂H₅)₂-C₆H₄ | C₆H₄ | 4-N(C₂H₅)₂-C₆H₄ | 4-N(C₂H₅)₂-C₆H₄ | H | H | H | isoxazole |

TABLE 12

[Compounds represented by the formula (2)]

| Compound | Ar¹ | Ar² | Ar³ | Ar⁴ | Ar⁵ | Ar⁶ | R¹ | R² | R⁵ | Z¹ |
|---|---|---|---|---|---|---|---|---|---|---|
| 72 | phenyl | 4-(N,N-dimethylamino)phenyl | 4-(N,N-dimethylamino)phenyl | phenyl | 4-(N,N-dimethylamino)phenyl | 4-(N,N-dimethylamino)phenyl | H | H | H | H |
| 73 | phenyl | 1-naphthyl | 1-naphthyl | phenyl | 2-naphthyl | 2-naphthyl | H | H | H | H |
| 74 | phenyl | 2-methylbiphenyl | 2-methylbiphenyl | phenyl | 2-methylbiphenyl | 2-methylbiphenyl | H | H | H | H |
| 75 | naphthyl | 3,5-dimethylphenyl | 3,5-dimethylphenyl | naphthyl | 3,5-dimethylphenyl | 3,5-dimethylphenyl | H | H | H | H |
| 76 | naphthyl | 4-(N,N-diethylamino)phenyl | 4-(N,N-diethylamino)phenyl | naphthyl | 4-(N,N-diethylamino)phenyl | 4-(N,N-diethylamino)phenyl | H | H | H | H |
| 77 | biphenyl | phenyl | phenyl | biphenyl | phenyl | phenyl | H | H | H | H |

TABLE 13

| Compound | Ar¹ | Ar² | Ar³ | Ar⁴ | Ar⁵ | Ar⁶ | R¹ | R² | Z² | Z³ |
|---|---|---|---|---|---|---|---|---|---|---|
| 78 | C₆H₄ | C₆H₄-CH₃ | C₆H₄-CH₃ | C₆H₄ | C₆H₄-CH₃ | C₆H₄-CH₃ | H | H | furan | furan |
| 79 | biphenyl | C₆H₅ | C₆H₅ | biphenyl | C₆H₅ | C₆H₅ | H | H | furan | thiophene |
| 80 | C₆H₄ | 1,4,5,8-tetramethylnaphthyl | 1-methylnaphthyl | C₆H₄ | 1-methylnaphthyl | 1-methylnaphthyl | H | H | furan | furan |
| 81 | C₆H₄ | C₆H₄-CH₃ | C₆H₄-CH₃ | C₆H₄ | C₆H₄-CH₃ | C₆H₄-CH₃ | H | H | furan | isoxazole |
| 82 | C₆H₄-CH₃ | C₆H₄-N(CH₃)₂ | C₆H₄-N(CH₃)₂ | C₆H₄ | C₆H₄-N(CH₃)₂ | C₆H₄-N(CH₃)₂ | H | H | thiophene | thiophene |
| 83 | naphthyl | C₆H₄-N(CH₃)₂ | C₆H₄-N(CH₃)₂ | naphthyl | C₆H₄-N(CH₃)₂ | C₆H₄-N(CH₃)₂ | H | H | thiophene | thiophene |

TABLE 14

[Compounds represented by the formula (3)]

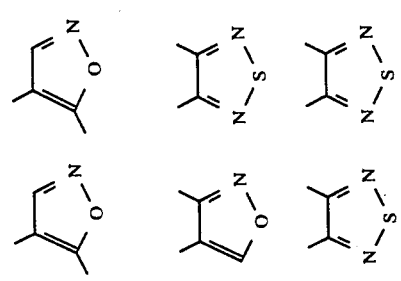

| Compound | Ar¹ | Ar² | Ar³ | Ar⁴ | Ar⁵ | Ar⁶ | R¹ | R² | Z² | Z³ |
|---|---|---|---|---|---|---|---|---|---|---|
| 84 | naphthyl | phenyl | phenyl | naphthyl | phenyl | phenyl | —CH₃ | —CH₃ | thiophene | isoxazole |
| 85 | naphthyl | phenyl | phenyl | naphthyl | phenyl | phenyl | H | H | thiophene | thiadiazole |
| 86 | naphthyl | 4-OCH₃-phenyl | 4-OCH₃-phenyl | naphthyl | 4-OCH₃-phenyl | 4-OCH₃-phenyl | H | H | isoxazole | isoxazole |
| 87 | phenyl | 4-CH₃-phenyl | 4-CH₃-phenyl | phenyl | 4-CH₃-phenyl | 4-CH₃-phenyl | H | H | isoxazole | isothiazole |
| 88 | naphthyl | 4-CH₃-phenyl | 4-CH₃-phenyl | naphthyl | 4-CH₃-phenyl | 4-CH₃-phenyl | H | H | thiadiazole | thiadiazole |

The compounds represented by the formulae (1), (2) and (3) are soluble in solvents such as tetrahydrofuran, chloroform, dichloromethane, dichloroethane and toluene. Each of these compounds is dissolved or dispersed in a binder resin, and the resultant solution is then used in a coating step to prepare a hard film having large mechanical strength. The thus prepared film is useful as a charge transport layer of an electrophotographic photosensitive element.

In the electrophotographic photosensitive element of the present invention, an undercoat layer, a charge generating layer and a charge transport layer are preferably formed in this order on a conductive substrate, but these layers may be laminated in the order of the undercoat layer, the charge generating layer and the charge transport layer. In addition, the charge generating material and the charge transport material may be dissolved/dispersed in the suitable resin and applied on the undercoat layer. If necessary, the undercoat layer can be omitted. Furthermore, if necessary, an overcoat layer may be additionally formed as the outermost layer.

Preferable examples of the conductive substrate include conductive metals such as aluminum and synthetic resins having conductive surfaces.

The charge transport layer having high charge carrier mobility, small residual surface potential and dark-decay ratio as well as good repeating stability can be obtained by coating a support such as the substrate with the compound as a charge transport material represented by the formula (1), (2) and (3), if necessary, together with the suitable binder resin. The coating can be carried out by the use of a usual coating device such as a spin coater, an applicator, a spray coater, a bar coater, an immersion coater, a doctor blade, a roller coater, a curtain coater, a bead coater or a slide hopper. Drying can be carried out preferably by heating at a temperature of from 40° to 300° C., preferably from 60° to 200° C. for a period of from 2 minutes to 10 hours, preferably from 10 minutes to 6 hours under rest or blow conditions.

The binder resin which is used in forming the charge transport layer by the coating can be selected from many usual insulating resins. Furthermore, the binder resin can also be selected from organic photoconductive polymers such as polyvinyl carbazole resins, polyvinyl anthracene resins and polyvinyl pyrene resins. Typical examples of the binder resin include polyvinyl butyral resins, polyallylate resins, polycarbonate resins, polyester resins, polyester carbonate resins, phenoxy resins, polyvinyl acetate resins, acrylic resins, polyacrylamide resins, polyamide resins, polyvinyl pyridine resins, cellulosic resins, urethane resins, epoxy resins, silicon resins, polystyrene resins, polyether resins, polythioether resins, polyketone resins, polyvinyl chloride resins, vinyl chloride-vinyl acetate copolymers, polyvinyl acetal resins, polyacrylonitrile resins, phenolic resins, melamine resins, caseins, polyvinyl alcohol resins, polyvinyl pyrrolidone resins and polysilanes. These resins are not restrictive. The amount of the resin contained in the charge transport layer is from 99% by weight to 0% by weight, preferably 70% by weight to 30% by weight based on the total weight of the charge transport layer. These resins may be used singly or in a combination of two or more thereof.

A solvent which is used to dissolve the charge transport material depends upon the kind of resin and the like, but it is preferred to select the solvent from compounds not having an influence on the undermentioned charge generating layer and the undercoat layer at the time of the coating.

Typical examples of the solvent include aromatic hydrocarbons such as benzene, toluene, xylene, ligroin, monochlorobenzene and dichlorobenzene, ketones such as acetone, methyl ethyl ketone and cyclohexanone, alcohols such as methanol, ethanol and isopropanol, esters such as ethyl acetate and methyl cellosolve, aliphatic halogenated hydrocarbons such as carbon tetrachloride, chloroform, dichloromethane, dichloroethane and trichloroethylene, ethers such as tetrahydrofuran and dioxane, amides such as N,N-dimethylformamide and N,N-dimethylacetamide, and sulfoxides such as dimethyl sulfoxide. These solvents are not restrictive.

The thickness of the charge transport layer in the electrophotographic photosensitive element is preferably from 5 to 50 $\mu$m, more preferably from 10 to 30 $\mu$m. To this charge transport layer, there may be added various usual additives such as an ultraviolet absorber, an antioxidant, an electron absorbing material and a plasticizer, if necessary.

Examples of the charge generating material include known photoconductive materials, for example, inorganic materials such as CdS, Se, ZnO and a-Si, phthalocyanines each having a metallic atom such as Si, Ge, Co, Cu, Al, In, Ti, Pb or V in the molecule, metal-free phthalocyanines, and organic materials such as azo pigments, bisazo pigments, trisazo pigments, polycyclic quinone pigments, perylene pigments, cyanine dyes and squarium dyes. These materials can be used singly or in the form of a mixture thereof.

As a binder resin which can be mixed with the above-mentioned charge generating material, if necessary, in forming the charge generating layer, there can be used the binder resin which can be used in the above-mentioned charge transport layer, if necessary.

The content of the binder resin in the charge generating layer is preferably from 0 to 99% by weight, more preferably from 20 to 80% by weight based on the total weight of the charge generating layer.

A solvent which is used to dissolve the charge generating material and the binder resin depends upon the kind of resin and the like, but it is preferred to select the solvent from compounds not having an influence on the undermentioned undercoat layer at the time of the coating. Typical examples of the solvent include aromatic hydrocarbons such as benzene, toluene, xylene, ligroin, monochlorobenzene and dichlorobenzene, ketones such as acetone, methyl ethyl ketone, methyl isobutyl ketone and cyclohexanone, alcohols such as methanol, ethanol and isopropanol, esters such as ethyl acetate and methyl cellosolve, aliphatic halogenated hydrocarbons such as carbon tetrachloride, chloroform, dichloromethane, dichloroethane and trichloroethylene, ethers such as tetrahydrofuran and dioxane, amides such as N,N-dimethylformamide and N,N-dimethylacetamide, and sulfoxides such as dimethyl sulfoxide.

Furthermore, the thickness of the charge generating film is preferably from 0.01 to 2 $\mu$m, more preferably from 0.1 to 1 $\mu$m in order to maintain charging properties and to secure stability. If necessary, a plasticizer, an electron acceptor, an electron donor and the like can be used together with the binder. Coating can be carried out in the same manner as in the case of the above-mentioned charge transport layer.

As the binder resin which can be used for the undercoat layer, any usual resin can be used. Examples of the binder resin include alcohol-soluble polyamide resins such as 6-nylon, 6,6-nylon, 11-nylon, 6,10-nylon, co-polymer nylon and alkoxymethylated nylon, casein, polyvinyl alcohol resins, ethylene-acrylic acid copolymers, vinyl chloridevinyl acetate-maleic acid copolymers, epoxy resins, gelatin, polyurethane resins and polyvinyl butyral resins, and cellulosic resins such as nitrocellulose and carboxymethylcellulose. These resins may be used singly or in the form of a mixture thereof. If necessary, an electron acceptor or an electron donor may be used. The coating of the undercoat layer can be carried out in the same manner as in the case of the above-mentioned charge transport layer and charge generating layer. In this case, the thickness of the undercoat layer is from 0.01 to 20 μm, preferably from about 0.2 to 10 μm. Moreover, the undercoat layer can be omitted, if necessary.

The above-mentioned description can mainly be applied to the multi-layer type photosensitive element in which the charge generating layer and the charge transport layer are separately constituted, but it can also be applied to the single layer type photosensitive element in which the charge generating and the charge transport are effected in one layer.

In this case, a blend weight ratio of the compound of the formula (1), (2) or (3) to the charge generating material is preferably from 0.3:1 to 1:0.3.

The content of the binder resin is preferably from 0 to 90% by weight, more preferably from 20 to 60% by weight based on the total weight of the layer.

The electrophotographic photosensitive element of the present invention is used in a duplicating machine, a printer and a facsimile and it is also useful as an electrophotographic plate, a solar cell, a photoelectric conversion element such as an electroluminescent element, an optical conversion element and a material for optical discs.

With regard to the structure of the electrophotographic photosensitive element, various conformations are known, but the electrophotographic photosensitive element of the present invention can take any conformation. In general, the electrophotographic photosensitive element has any one of sectional structures shown in FIGS. 1 to 6. In FIGS. 1 and 2, a photosensitive layer 4 is shown in which a charge generating layer 2 containing a charge generating material as the main component and a charge transport layer 3 containing a charge transport material as the main component are laminated on a conductive support 1.

Figure 4:
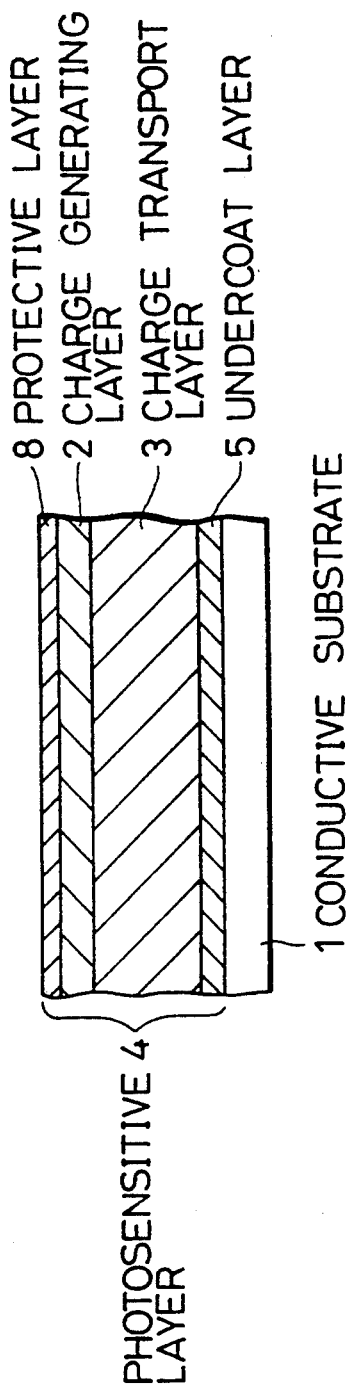

As shown in FIGS. 3 and 4, this photosensitive layer 4 may be provided via an undercoat layer 5 formed on the conductive support 1. When the photosensitive layer 4 is formed with a two-layer constitution in such a way, the photosensitive element having the most excellent electrophotographic properties can be obtained.

In the present invention, the photosensitive layer 4 in which a charge generating material 7 is dispersed in a layer 6 containing a charge transport material as the main component may be provided directly or via the undercoat layer 5 on the conductive support 1, as shown in FIGS. 5 and 6. Alternatively, in the present invention, a protective layer 8 may be provided as the outermost layer, as in FIG. 4.

The electrophotographic photosensitive element of the present invention has excellent photosensitive properties as well as small residual surface potential and darkdecay ratio, and the photofatigue of the element can be inhibited and thus it exerts good repeating stability.

Now, the present invention will be described in detail in reference to examples, but the scope of the present invention should not be limited to these examples.

EXAMPLE 1

An undercoat layer (thickness=0.1 μm) comprising methoxymethylated nylon (T-8, made by Unitika Ltd.) was formed on an aluminum substrate. Next, a charge generating layer (thickness=0.1 μm) comprising polyvinyl butyral (BX-1, made of Sekisui Chemical Co., Ltd.) containing 50% by weight of n-type titanyl oxide phthalocyanine was formed on the undercoat layer. Furthermore, the thus formed charge generating layer was coated with a dichloroethane solution of the exemplary compound (1) in Table 1 and a polycarbonate (Yupiron Z-200; made by Mitsubishi Gas Chemical Company, Inc.) (weight ratio=0.8:1), and the solution was then dried at 90° C. for 60 minutes to form a charge transport layer having a thickness of 20 μm. The coating properties of the resultant film were good, and the film had sufficient strength.

The evaluation of electrophotographic properties was made as follows: The above-mentioned photosensitive element was electrified under a corona discharge of −6 kV by the use of an electrostatic Paper Analyzer made by Kawaguchi Denki Co., Ltd., and it was then allowed to stand for 3 minutes and to darkdecay. Afterward, the photosensitive element was irradiated with white light of 5 luces for 5 seconds, and a time (second) till its surface potential became ½ was measured to obtain a half-exposure E½ (lux.second). The results are set forth in Table 15. In Table 15, −Vr is residual potential after the irradiation.

TABLE 15

|  | First time | | 1000th time | |
|---|---|---|---|---|
|  | (lux · sec) E½ | (V) −Vr | (lux · sec) E½ | (V) −Vr |
| Example 1 | 0.4 | −1 | 0.4 | −2 |

EXAMPLES 2 to 16

Photosensitive elements were prepared by the same procedure as in Example 1 except that the exemplary compound (1) used in Example 1 was replaced with exemplary compounds shown in Table 16, and half-exposures were then measured.

TABLE 16

|  | Exemplary Compound | First time | | 1000th time | |
|---|---|---|---|---|---|
|  |  | (lux · sec) E½ | (V) −Vr | (lux · sec) E½ | (V) −Vr |
| Example 2 | 3 | 0.4 | −1 | 0.4 | −2 |
| Example 3 | 10 | 0.3 | 0 | 0.3 | −1 |
| Example 4 | 11 | 0.3 | 0 | 0.3 | −2 |
| Example 5 | 15 | 0.5 | 0 | 0.5 | −1 |
| Example 6 | 20 | 0.3 | 0 | 0.3 | −1 |
| Example 7 | 27 | 0.4 | −1 | 0.4 | −2 |
| Example 8 | 28 | 0.3 | −1 | 0.3 | −3 |
| Example 9 | 30 | 0.5 | −1 | 0.5 | −2 |
| Example 10 | 50 | 0.3 | 0 | 0.3 | −1 |
| Example 11 | 53 | 0.4 | 0 | 0.4 | −1 |
| Example 12 | 59 | 0.4 | −1 | 0.4 | −2 |
| Example 13 | 64 | 0.5 | −1 | 0.5 | −3 |
| Example 14 | 72 | 0.4 | 0 | 0.4 | −1 |
| Example 15 | 77 | 0.3 | 0 | 0.3 | −1 |
| Example 16 | 81 | 0.5 | 0 | 0.5 | −1 |

COMPARATIVE EXAMPLE 1

A photosensitive element for comparison was prepared by the same procedure as in Example 1 except that a compound represented by the chemical formula (6) was used as a charge transport material. The resultant electrosensitive element for comparison was evaluated in the same manner as in Example 1, and the results are set forth in Table 17.

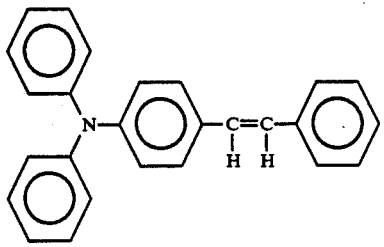
(6)

TABLE 17

|  | First time | | 1000th time | |
|---|---|---|---|---|
|  | (lux·sec) $E_{\frac{1}{2}}$ | (V) $-V_r$ | (lux·sec) $E_{\frac{1}{2}}$ | (V) $-V_r$ |
| Comp. Ex. 1 | 0.5 | −10 | 0.6 | −25 |

EXAMPLE 17

An undercoat layer (thickness=0.1 μm) comprising a polyamide resin (A-70, made by Toray Industries, Inc.) was formed on a conductive support obtained by vapor-depositing aluminum on a polyester film, and a charge generating layer (thickness=0.1 μm) comprising a butyral resin (Denka Butyral #3000, made by Denki Kagaku Kogyo K.K.) containing 50% by weight of a τ-type metal-free phthalocyanine was formed on the undercoat layer. The exemplary compound (2) in Table 1 was used as a charge transport material, and 1.5% by weight of an antioxidant (Irganox 1010, made by Japanese Ciba-Geigy) were added to the charge transport material, followed by the same procedure as in Example 1, to prepare a photosensitive element. This photosensitive element was also evaluated in the same manner as in Example 1, and the results are set forth in Table 18.

TABLE 18

|  | First time | | 1000th time | |
|---|---|---|---|---|
|  | (lux·sec) $E_{\frac{1}{2}}$ | (V) $-V_r$ | (lux·sec) $E_{\frac{1}{2}}$ | (V) $-V_r$ |
| Example 17 | 1.3 | 0 | 1.4 | −1 |

EXAMPLES 18 to 31

Photosensitive elements were prepared by the same procedure as in Example 17 except that the exemplary compound (2) used in Example 17 was replaced with exemplary compounds shown in Table 19, and half-exposures were then measured.

TABLE 19

| Exemplary Compound | First time | | 1000th time | |
|---|---|---|---|---|
|  | (lux·sec) $E_{\frac{1}{2}}$ | (V) $-V_r$ | (lux·sec) $E_{\frac{1}{2}}$ | (V) $-V_r$ |
| Example 18 | 8 | 2.4 | −1 | 2.4 | −2 |
| Example 19 | 11 | 2.3 | 0 | 2.3 | −1 |
| Example 20 | 16 | 2.4 | 0 | 2.4 | −2 |
| Example 21 | 20 | 2.2 | −1 | 2.2 | −1 |
| Example 22 | 24 | 2.3 | 0 | 2.3 | −1 |
| Example 23 | 29 | 2.4 | −1 | 2.4 | −2 |
| Example 24 | 36 | 2.3 | −1 | 2.5 | −3 |
| Example 25 | 50 | 2.1 | −1 | 2.1 | −2 |
| Example 26 | 55 | 2.3 | 0 | 2.3 | −1 |
| Example 27 | 67 | 2.4 | 0 | 2.4 | −1 |
| Example 28 | 71 | 2.4 | 0 | 2.4 | −1 |
| Example 29 | 74 | 2.5 | −2 | 2.5 | −3 |
| Example 30 | 76 | 2.4 | 0 | 2.4 | −1 |
| Example 31 | 79 | 2.2 | 0 | 2.2 | 0 |
| Example 32 | 89 | 2.3 | 0 | 2.3 | −1 |

COMPARATIVE EXAMPLE 2

A photosensitive element for comparison was prepared by the same procedure as in Example 17 except that a compound represented by the chemical formula (7) was used as a charge transport material. The resultant photosensitive element for comparison was evaluated in the same manner as in Example 17, and the results are set forth in Table 20.

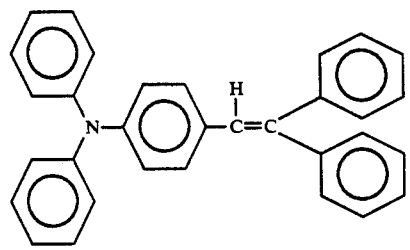
(7)

TABLE 20

|  | First time | | 1000 time | |
|---|---|---|---|---|
|  | (lux·sec) $E_{\frac{1}{2}}$ | (V) $-V_r$ | (lux·sec) $E_{\frac{1}{2}}$ | (V) $-V_r$ |
| Comp. Ex. 2 | 4.0 | −10 | 5.0 | −30 |

What is claimed is:

1. An electrophotographic photosensitive element comprising a conductive substrate and at least a photosensitive layer formed on the conductive substrate, said electrophotographic photosensitive element being characterized in that the photosensitive layer contains, as a charge transport material, a compound represented by the formula (1)

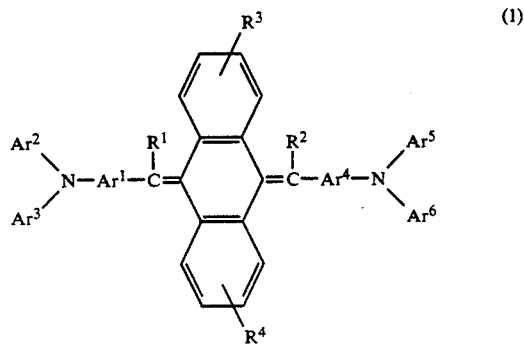
(1)

wherein each of $Ar^1$, $Ar^2$, $Ar^3$, $Ar^4$, $Ar^5$, and $Ar^6$ is a mono or disubstituted or non-substituted aromatic or heterocyclic group with the proviso that when simultaneously $Ar^1$ and $Ar^4$ are phenylene, simultaneously $Ar^2$, $Ar^3$, $Ar^5$, and $Ar^6$ are not all phenyl groups or phenylene groups; and each of $R^1$, $R^2$, $R^3$, and $R^4$ is a substituted or non-substituted aromatic or heterocyclic group, a hydrogen atom, a halogen atom, a hydroxyl group, a substituted or non-substituted amino group, a lower alkoxy group having 1 to 6 carbon atoms which may have a substituent, or a lower alkyl group having 1 to 6 carbon atoms which may have a substituent.

2. An electrophotographic photosensitive element comprising a conductive substrate and at least a photosensitive layer formed on the conductive substrate, said electrophotographic photosensitive element being characterized in that the photosensitive layer contains, as a charge transport material, a compound represented by the formula (2)

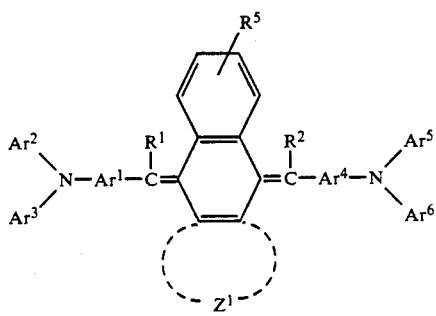

(2)

(wherein —$Z^1$— is two hydrogen atoms, or a disubstituted or non-substituted heterocyclic group; each of $Ar^1$, $Ar^2$, $Ar^3$, $Ar^4$, $Ar^5$ and $Ar^6$ is a mono or disubstituted or non-substituted aromatic or heterocyclic group; and each of $R^1$, $R^2$ and $R^5$ is a substituted or non-substituted aromatic or heterocyclic group, a hydrogen atom, a halogen atom, a hydroxyl group, a substituted or non-substituted amino group, a lower alkoxy group having 1 to 6 carbon atoms which may have a substituent, or a lower alkyl group having 1 to 6 carbon atoms which may have a substituent.

3. An electrophotographic photosensitive element comprising a conductive substrate and at least a photosensitive layer formed on the conductive substrate, said electrophotographic photosensitive element being characterized in that the photosensitive layer contains, as a charge transport material, a compound represented by the formula (3)

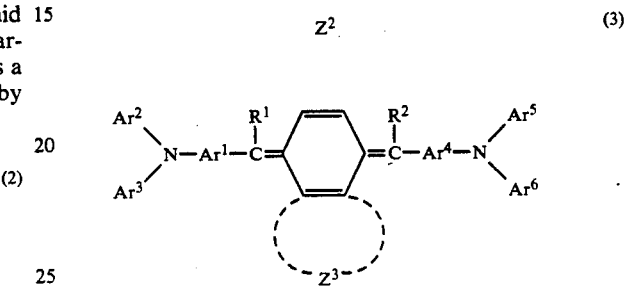

(3)

wherein each of —$Z^2$— and —$Z^3$— is a disubstituted or non-substituted heterocyclic group; each of $Ar^1$, $Ar^2$, $Ar^3$, $Ar^4$, $Ar^5$ and $Ar^6$ is a mono or disubstituted or non-substituted aromatic or heterocyclic group; and each of $R^1$ and $R^2$ is a substituted or non-substituted aromatic or heterocyclic group, a hydrogen atom, a halogen atom, a hydroxyl group, a substituted or non-substituted amino group, a lower alkoxy group having 1 to 6 carbon atoms which may have a substituent, or a lower alkyl group having 1 to 6 carbon atoms which may have a substituent.

* * * * *